(12) United States Patent
Rossiger

(10) Patent No.: US 9,880,329 B2
(45) Date of Patent: Jan. 30, 2018

(54) OPTICAL MIRROR, X-RAY FLUORESCENCE ANALYSIS DEVICE, AND METHOD FOR X-RAY FLUORESCENCE ANALYSIS

(71) Applicant: Helmut Fischer GmbH Insitut fur Elektronik und Messtechnik, Sindelfingen (DE)

(72) Inventor: Volker Rossiger

(*) Notice: Subject to any disclaimer, the term of this patent is extended or adjusted under 35 U.S.C. 154(b) by 193 days.

(21) Appl. No.: 14/761,493

(22) PCT Filed: Feb. 27, 2014

(86) PCT No.: PCT/EP2014/053799
§ 371 (c)(1),
(2) Date: Jul. 16, 2015

(87) PCT Pub. No.: WO2014/135429
PCT Pub. Date: Sep. 12, 2014

(65) Prior Publication Data
US 2015/0362639 A1 Dec. 17, 2015

(30) Foreign Application Priority Data
Mar. 7, 2013 (DE) .................. 10 2013 102 270

(51) Int. Cl.
*G01N 23/223* (2006.01)
*G02B 5/08* (2006.01)
(Continued)

(52) U.S. Cl.
CPC .......... *G02B 5/0808* (2013.01); *G01B 15/02* (2013.01); *G01N 23/223* (2013.01); *G01N 23/2206* (2013.01); *G01N 2223/076* (2013.01)

(58) Field of Classification Search
CPC ...... G01N 23/00; G01N 23/02; G01N 23/043; G01N 23/22; G01N 23/223;
(Continued)

(56) References Cited

U.S. PATENT DOCUMENTS 4,406,015 A    9/1983  Koga
5,247,395 A *  9/1993  Martinez .................. G02B 5/08
                                                     156/229
(Continued)

FOREIGN PATENT DOCUMENTS

DE    33 14 281 A1    10/1984
GB    2 095 960 A     10/1982

OTHER PUBLICATIONS

International Search Report for corresponding patent application No. PCT/EP2014/053799 dated Apr. 22, 2014.

*Primary Examiner* — Jurie Yun
(74) *Attorney, Agent, or Firm* — Renner, Otto, Boisselle & Sklar, LLP

(57) ABSTRACT

An x-ray fluorescence analysis device, including an x-ray source for irradiating a sample with x-ray radiation, an x-ray detector for measuring x-ray fluorescence radiation emitted by the sample, and a camera for producing an optical control image of the irradiated measurement point of a sample by means of an optical mirror arranged at an angle in the beam path of the x-ray source, which optical mirror includes a carrier having a mirror layer provided on the carrier. In order to create an x-ray florescence device by means of which realistic control recordings of the sample to be analyzed, in particular of the sampled surface point, the optical mirror has a passage window for the x-ray radiation, which is formed by an opening in the carrier and a foil forming the mirror layer and covering the opening on an outer surface of the carrier.

15 Claims, 2 Drawing Sheets

Figure 1:
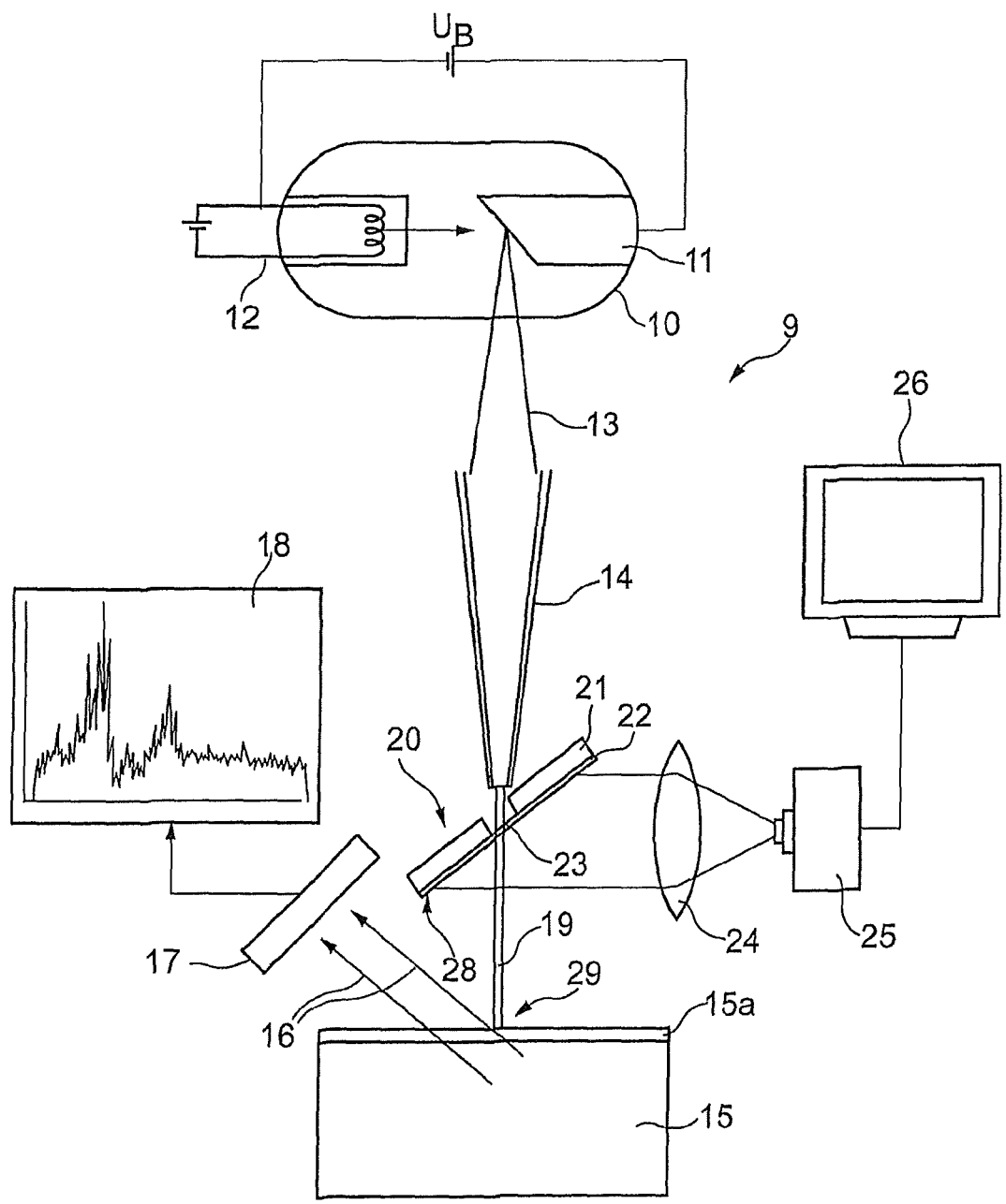

(51) Int. Cl.
*G01B 15/02* (2006.01)
*G01N 23/22* (2006.01)

(58) Field of Classification Search
CPC ......... G01N 23/2206; G01N 2223/076; G01B 15/02; G02B 5/08; G02B 5/0808
USPC ...................................... 378/44, 45, 50, 205
See application file for complete search history.

(56) References Cited

U.S. PATENT DOCUMENTS

| | | |
|---|---|---|
| 2005/0069092 A1 | 3/2005 | Xiaodong et al. |
| 2009/0190722 A1 | 7/2009 | Windt |
| 2013/0168570 A1* | 7/2013 | Wendler .................. A61B 6/037 250/395 |

* cited by examiner

OPTICAL MIRROR, X-RAY FLUORESCENCE ANALYSIS DEVICE, AND METHOD FOR X-RAY FLUORESCENCE ANALYSIS

The present invention relates to an optical mirror, in particular for an x-ray fluorescence analysis device, as well as an x-ray fluorescence analysis device having an x-ray source for radiation of the sample with x-ray radiation, an x-ray detector for the measurement of the x-ray fluorescence radiation emitted by the sample and a camera for the generation of an optical image of the radiated position of the sample via an optical mirror which is arranged at an angle in the beam path of the x-ray source. Furthermore, the invention relates to a corresponding method for x-ray fluorescence analysis, in particular to determine the thickness of thin layers.

The x-ray fluorescence analysis is a disruption-free method for qualitative and quantitative material analysis. It is based on the principle that electrons are liberated from the inner shells of the atoms forming the sample by radiation of a sample with polychromatic x-ray radiation. The gaps existing therein are filled by electrons from the outer shells. During these transfers, characteristic fluorescence radiation in the x-ray range occurs which is recorded by a detector and provides information about the elementary composition of the sample.

The x-ray fluorescence analysis is, in particular, also used for layer thickness measurement of thin layers and layer systems. As x-ray radiation penetrates thin layers, x-ray fluorescence radiation is also generated in the material lying thereunder, which is in turn weakened by absorption in the layers lying above this on its way to the detector. Both the material composition and the present layer thickness can be determined by evaluating the spectrum in the range of the wavelengths of x-ray radiation. In order to achieve a good spatial resolution, the measurement spot, so the region of the sample detected by the primary radiation, must be selected to be quite small.

In the study of samples by means of x-ray fluorescence analysis, it is necessary to adjust the measurement spot via an optical image of the sample surface. This occurs, as a rule, using a camera. In order to generate a parallax-free image of a measurement position of the sample, the control shot must, however, be taken as much in parallel to the x-ray beam as possible. For this purpose, an optical mirror is arranged in the beam path at an angle to which the camera is directed. However, so that the mirror does not absorb the x-ray beam on its way to the measurement position, this has a hole in the passage region of the x-ray beam. Such an optical mirror is known from DE 33 14 281 A1. This optical mirror, however, has the disadvantage that it must be fixed at a long distance from the sample surface in order to generate an undisturbed image.

An x-ray fluorescence analysis device, in which a mirror having a hole for the passage of the x-ray beam is used to generate a control shot, is, for example, known from DE 197 10 420 A1. In EP 1 348 949 B1, focusing x-ray optics are additionally used which are guided through a recess in the control mirror. The same thing is known from DE 32 39 379 C2, which discloses a mirror wherein the size of the hole is able to be adjusted for the passage of the x-ray beam.

Furthermore, an x-ray fluorescence analysis device as well as a method for x-ray fluorescence analysis are known from U.S. Pat. No. 4,406,015A, in which a mirror is arranged in the primary beam, said mirror having an aluminium layer which is vapour deposited on an $SiO_2$ plate or an aluminium layer which is vapour deposited on a plastic film. The mirror therefore comprises a full-surface aluminium layer on a full-surface carrier formed from plastic or a full-surface $SiO_2$ plate.

Both embodiments have the disadvantage that these full-surface carriers reduce the intensity of the x-ray radiation directed towards the measurement object, whereby higher measurement times are required. Additionally, the embodiment having the carrier consisting of plastic has the disadvantage that, over the course of time, this plastic is corroded due to the radiation by means of x-ray radiation.

The object of the invention is to improve an optical mirror, an x-ray fluorescence analysis device as well as a method for x-ray fluorescence analysis to the effect that natural control shots are possible at the measurement position of the sample to be analysed and when this is situated at a very short distance to the mirror.

The object is solved by the features of claims 1, 9 and 12. Advantageous embodiments are to be gleaned from the dependent claims.

The object is solved by an optical mirror which has a passage window for the x-ray radiation, which is formed by a recess in the carrier, and a film which covers the recess and which forms the mirror layer. Such an optical mirror is, on the one hand, permeable for the x-ray radiation, in particular the primary radiation of the x-ray radiation, with a high intensity, as only the film is penetrated, and is impermeable for the optical radiation to detect an image of the surface of the measurement position of the sample such that a complete image of the measurement position is able to be detected by a camera.

Miniature optics can be created by such an optical mirror, whereby the distance between a focal point on the sample and x-ray optics can be kept low by retention of the positions of the optical mirror for direct observation of the sample. Therefore a compact or space-saving construction of an x-ray fluorescence device is achieved.

Preferably, the film is produced from a plastic, particularly preferably from polyethylene terephthalate. Plastics mainly consist of carbon having an atomic number of only 6. As the x-ray absorption has a very strong dependency on the atomic number z of the material to be penetrated (approx. $\sim z^4$), weakening by a plastic film is very low. Extremely tear-resistant films can be produced from polyethylene terephthalate, PET in short, in particular if such a film is biaxially stretched.

In order to obtain a reflective coating on the film or to form a mirror layer, the film can be metallised. A metallisation can, for example, be produced in a simple manner by sputtering (cathode atomisation) or vacuum depositing.

Preferably, a mirror coating made from aluminium is applied, as aluminium has the lowest atomic number of the metals which are considered for mirroring and can furthermore be very well sputtered.

Such a film which is applied to the carrier can be implemented to be extremely thin, for example having a thickness of only a few micrometers, such that the primary x-ray radiation, the absorption of which depends exponentially on the thickness of the material to be penetrated, is hardly weakened.

In order for a stable optical mirror to be obtained, the carrier has a planar base body which preferably consists of glass which has a recess, preferably a round hole, in the region of the passage window. The mirrored film can be spread or glued onto the carrier, wherein the glue points only need to be provided, for example, in the edge region.

In particular, a tension-free arrangement of the film in the region of the recess in the carrier can be achieved by gluing the film onto the carrier. Therefore, only the film is active in the region of the penetration of the mirror which, however, hardly causes an identity loss of the x-ray radiation.

Alternatively, the optical mirror can also have a frame as a carrier, onto or over which the mirrored film is spread.

Furthermore, the object of the invention is solved by an x-ray fluorescence analysis device in which an optical mirror having a passage window for the x-ray radiation is used which comprises a carrier having a recess which is covered with a film which forms the mirror layer on an outer side of the carrier.

An optical image can thereby be detected by the measurement position of the sample, which can be analysed for the control of the measurement.

An endoscope can be used as the camera, for example a video endoscope. Focusing x-ray optics are used due to the compact construction type achieved in this way and is positioned very close to the sample surface. A very good spatial resolution is hereby achieved.

Preferably a mono- or polycapillary lens is positioned in front of the mirror, seen in the beam direction, in order to focus the primary beam and to achieve a smaller measurement spot on the measurement surface.

Furthermore, the object of the invention is solved by a method for x-ray fluorescence analysis of a sample, in which an optical mirror has a carrier having a passage window, such as, for example, a through-hole or recess, for the x-ray radiation, which is covered on an outer side of the carrier by a film which forms a mirror surface, such that only the film of the optical mirror is penetrated by x-ray radiation and a complete and distortion-free optical image is reflected by the measurement position or sample surface of the sample at the film which is formed as a mirror layer, and is detected by the camera. Therefore, improved evaluation and monitoring of the measurement at the measurement position of the sample can be achieved. Additionally, moving of the sample between an x-ray beam and a mirror positioned adjacent to this for the detection of a complete image of the measurement position of the sample is not required. This is because the optical mirror can be formed as space-saving optics and can remain between the x-ray radiation and the measurement position during a measurement.

Figure 2:
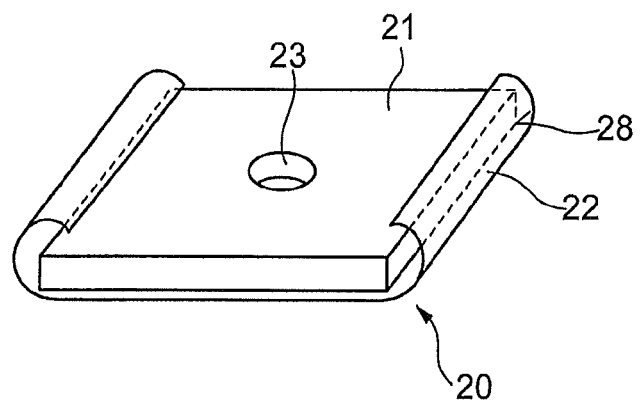
Figure 3:
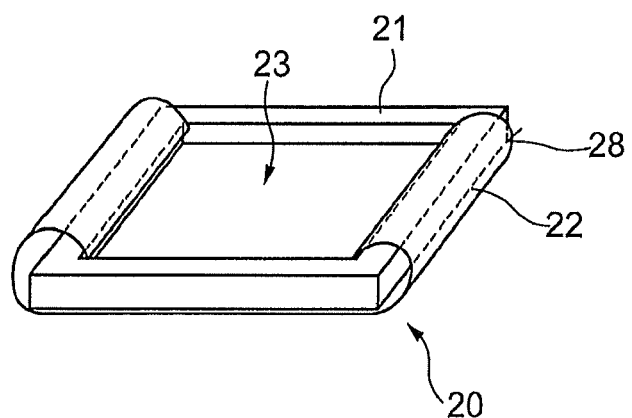

The invention as well as further advantageous embodiments and developments of the same are described and explained in more detail below by means of the examples depicted in the drawings. The features to be gleaned from the description and the drawings can be applied individually or together in any combination according to the invention. Here are shown:

FIG. 1 a schematic depiction of an x-ray fluorescence analysis device having an optical mirror according to the invention, FIG. 2 an isometric view of the optical mirror in a first embodiment, and FIG. 3 an isometric view of the optical mirror in a second embodiment.

The x-ray fluorescence analysis device 9 shown in FIG. 1 has an x-ray tube 10 of usual construction having a hot cathode 12 as an x-ray source, from which electrons are emitted and are accelerated using an acceleration voltage $U_B$ against an anode 11. There, the electrons are braked and generate x-ray radiation 13. The wavelength range of the polychromatic x-ray radiation 13 depends on the acceleration voltage $U_B$ which typically ranges from around 10 kV, for example in the exemplary embodiment at 50 kV, and the anode material, for example tungsten.

The x-ray radiation 13 is then preferably focused by x-ray optics 14 which are formed in the exemplary embodiment by a mono or polycapillary lens. Alternatively, only a simple collimator can also be used to fade out a beam 19.

The faded out or focused beam bundle 19 then strikes a sample 15. The sample 15 comprises, for example, a layer 15a or a layer system. The beam bundle 19 at least partially penetrates the layer 15a or penetrates through the upper layer 15a or the layer system of the sample 15. In the radiated region, x-ray fluorescence radiation 16 is generated which is measured by an x-ray detector 17, for example a semi-conductor detector. The material composition of the sample 15 and/or the layer thickness of the layer(s) 15a or the layer system can be determined using an evaluation of a measured energy spectrum 18 of the x-ray fluorescence radiation 16 in a way that is known in itself.

At the same time, the x-ray fluorescence analysis device enables a direct video observation of the sample surface at the measurement position 29. This serves for the control and simplifies, for example, the positioning of the sample 15 with respect to the measurement position. Furthermore, an optical control shot of the sampled region or of the measurement position 29 can thus be stored for each x-ray fluorescence measurement in order to later be able to comprehend the location of the measurement position 29 faultlessly.

In order for a parallax-free control shot to be able to be generated, the image of the measurement position 29 is captured in parallel to the x-ray beam 19. For this purpose, an optical mirror 20 is arranged at an angle in the beam path. Imaging optics, here a lens 24, display the mirror image of the sample surface of the measurement position 29 on a camera 25, for example a digital CCD camera. Preferably, an endoscope camera is provided which has small dimensions and is able to be positioned at a short distance from the optical mirror. The image of the camera 25 is depicted on a monitor 26 and can be stored and analysed with a measurement data set.

In order for the optical mirror 20 to weaken the x-ray beam 13 as little as possible, this has a passage window 30 for the x-ray beam 13. This passage window 30 is formed by a recess 23 in the carrier 21 which is covered on one side of the carrier 21 by a penetrating film 22 as a mirror layer 28. The outer side of the film 27 is mirrored. The carrier 21 is aligned in an inclined manner to the measurement position 29 with this mirrored outer side of the film 22 such that the x-ray radiation 13 enters and passes through firstly into the recess 23 of the carrier 21 and subsequently penetrates the film 22 or passes through the film 22. The carrier 21 preferably consists of glass.

The absorption of x-ray radiation on the one hand has an exponential dependency on the material thickness to be penetrated, and on the other hand has a very strong dependency proportionally to the fourth power of the atomic number Z of the penetrated material. Glass can indeed be used as a carrier material for the mirror 20 (silicon has an atomic number of 14), but the x-ray beam 13 can pass through the recess 23 unhindered.

A continuous, thin film 22, preferably made from plastic, is situated on the lower side of the optical mirror 20 which faces towards the camera 25. The plastics consist substantially of carbon, which has an atomic number of 6. Additionally, plastic films can be produced to be extremely thin, in the range of a few micrometers, but are nevertheless very durable and tear-resistant. A preferred plastic for the production of the film 22 is polyethylene terephthalate, PET in short. In particular, biaxially orientated polyester films made from PET, which are known by the names Mylar, Melinex or Hostaphan, are suitable for use according to the invention.

For the mirroring, the plastic film 22 is metallised in that, for example, a mirroring metallic coating is applied to the film by sputtering (cathode atomisation) or vacuum depositing. Because of the as small as possible atomic number, aluminium (atomic number 13) is particularly suitable as a coating material which can still be particularly well sputtered.

Metallised PET films which are suitable for the present use have a typical material thickness of, for example, less than 100 µm and have a high level of tear-resistance. The thickness of the reflective metallic coating can be less than 100 nm. Due to the extremely low material thickness of the metallised film 22 and the low atomic number thereof, it is virtually transparent for the x-ray radiation 13. It therefore also succeeds in creating a continuous optical mirror 20 having a virtually transparent passage window 30.

The film 22 can be glued, laminated or spread onto the flat base body of the carrier 21. The glue points can therein be restricted to the edge region of the carrier 21. In FIG. 2, such a mirror 20 is shown by way of example. The carrier 21 has a round hole as a passage widow 30, through which an x-ray beam 13 can pass. The film 22 is spread on an outer side of the carrier 21 and covers the hole 23.

Instead of a carrier 21 made from a glass plate having a round hole, the carrier 21 can also be implemented as only a rectangular frame, over which the film 22 is spread. Such an embodiment having a frame 21 as a carrier is shown in FIG. 3 by way of example. This embodiment has the advantage that a larger region is available as a passage window 30, such that the x-ray optics can be moved for scanning the measurement position 29 relative to the sample 15, instead of moving the sample 15 under the x-ray optics 14.

The distance between the x-ray optics 14 and the sample 15 amounts, in the exemplary embodiment, to approximately 15 mm. Larger distances are possible, but lead to poorer focusing of the x-ray beam 13 and therefore to a poorer spatial resolution of the x-ray fluorescence analysis device 9. Because of the small dimensions, a video endoscope is particularly suitable in which the imaging optics 24 and digital camera 25 are integrated in the form of an endoscope.

The features described above are each significant to the invention in themselves and are able to be combined with one another in any way.

The invention claimed is:

1. An optical mirror for an x-ray fluorescence analysis device having an x-ray source for irradiating a sample with x-ray radiation at a measurement position, an x-ray detector for the measurement of x-ray fluorescence radiation emitted by the sample, and a camera to generate an optical control image of the irradiated measurement position of the sample via the optical mirror which is arranged at an angle in the beam path of the x-ray source, which comprises a carrier having a mirror layer provided on the carrier,
wherein the optical mirror has a passage window for the x-ray radiation which is formed from a recess in the carrier and a film which covers the recess on an outer side of the carrier and which forms the mirror layer;
wherein the carrier has a planar base body, which has the recess in the region of the passage window; and
wherein the film is glued to the carrier and covers the recess of the carrier in a tension-free manner.

2. The optical mirror according to claim 1, wherein the film includes plastic.

3. The optical mirror according to claim 2, wherein the film includes polyethylene terephthalate.

4. The optical mirror according to claim 1, wherein the film is metallised.

5. The optical mirror according to claim 4, wherein the film has a coating made from aluminium.

6. The optical mirror according to claim 1, wherein the film has a thickness in a range of a few micrometers.

7. The optical mirror according to claim 1, wherein the carrier has a frame onto or over which the film is spread.

8. An x-ray fluorescence analysis device having an x-ray source for irradiating a sample with x-ray radiation at a measurement position, an x-ray detector for the measurement of the x-ray fluorescence radiation emitted by the sample, and a camera to generate an optical control image of the irradiated measurement position of the sample via an optical mirror which is arranged at an angle in the beam path of the x-ray source, which comprises a carrier having a mirror layer provided on the carrier, wherein the optical mirror is formed according to claim 1.

9. The x-ray fluorescence analysis device according to claim 8, wherein the camera is implemented as an endoscope.

10. The x-ray fluorescence analysis device according to claim 8, wherein a mono- or polycapillary lens is arranged in front of the optical mirror.

11. The optical mirror according to claim 1, wherein the planar base body is made of glass.

12. The optical mirror according to claim 1, wherein the recess is a round hole.

13. A method for x-ray fluorescence analysis of a sample to determine the thicknesses of thin layers, comprising:
irradiating the sample at a measurement position with polychromatic x-ray radiation from an x-ray source,
measuring x-ray fluorescence radiation emitted by the sample using an x-ray detector, and
generating an optical control image of the irradiated measurement position of the sample using a camera via an optical mirror which is arranged at an angle in the beam path of the x-ray source and which comprises a carrier having a mirror layer provided on the carrier,
wherein the carrier has a passage window for the x-ray radiation which is covered by a film which forms the mirror layer on an outer side of the carrier,
wherein the carrier has a planar base body, which has a recess in the region of the passage window,
wherein the film is glued to the carrier and covers the recess of the carrier in a tension-free manner, and
wherein the film is penetrated by the x-ray radiation in the region of the recess of the carrier of the optical mirror and the optical image is reflected by the measurement position of the sample on the film and is detected by the camera.

14. An optical mirror for an x-ray fluorescence analysis device having an x-ray source for irradiating a sample with x-ray radiation at a measurement position, an x-ray detector for the measurement of x-ray fluorescence radiation emitted by the sample, and a camera to generate an optical control image of the irradiated measurement position of the sample via the optical mirror which is arranged at an angle in the beam path of the x-ray source, which comprises a carrier having a mirror layer provided on the carrier,
wherein the optical mirror has a passage window for the x-ray radiation which is formed from a recess in the carrier and a film which covers the recess on an outer side of the carrier and which forms the mirror layer;
wherein the carrier has a planar base body, which has the recess in the region of the passage window; and
wherein the planar base body is made of glass.

15. The optical mirror according to claim 14, wherein the film is glued to the carrier and covers the recess of the carrier in a tension-free manner.

\* \* \* \* \*